US006268120B1

(12) United States Patent
Platz et al.

(10) Patent No.: US 6,268,120 B1
(45) Date of Patent: Jul. 31, 2001

(54) ISOALLOXAZINE DERIVATIVES TO NEUTRALIZE BIOLOGICAL CONTAMINANTS

(75) Inventors: Matthew Stewart Platz, Columbus, OH (US); Raymond Paul Goodrich, Jr., Denver, CO (US)

(73) Assignee: Gambro, Inc., Lakewood, CA (US)

( * ) Notice: Subject to any disclaimer, the term of this patent is extended or adjusted under 35 U.S.C. 154(b) by 0 days.

(21) Appl. No.: 09/420,652

(22) Filed: Oct. 19, 1999

(51) Int. Cl.⁷ .......................... A01N 1/02; C07D 471/14; A61K 31/525
(52) U.S. Cl. .......................... 435/2; 544/251; 514/251
(58) Field of Search .......................... 544/251; 514/251; 435/2

(56) References Cited

U.S. PATENT DOCUMENTS

| | | | |
|---|---|---|---|
| Re. 32,874 | 2/1989 | Rock et al. ..................... 424/101 |
| 683,690 | 1/1901 | Johnson . | |
| 1,733,239 | 10/1929 | Roberts . | |
| 1,961,700 | 6/1934 | Moehler ..................... 167/3 |
| 2,056,614 | 10/1936 | Moehler ..................... 21/18 |
| 2,111,491 * | 3/1938 | Kuhn et al. ..................... 260/29 |
| 2,212,230 | 8/1940 | Goldmann ..................... 250/11 |
| 2,212,330 | 8/1940 | Thomas ..................... 250/52 |
| 2,340,890 | 2/1944 | Lang et al. . | |
| 2,654,735 * | 10/1953 | Funk et al. ..................... 260/211.3 |
| 2,825,729 * | 3/1958 | Petering et al. ..................... 260/251.5 |
| 3,189,598 * | 6/1965 | Yagi et al. ..................... 260/211.3 |
| 3,456,053 | 7/1969 | Crawford ..................... 424/89 |
| 3,683,177 | 8/1972 | Veloz ..................... 250/43 |
| 3,683,183 | 8/1972 | Vizzini et al. ..................... 250/44 |
| 3,705,985 | 12/1972 | Manning et al. ..................... 250/106 S |
| 3,776,694 | 12/1973 | Leittl ..................... 21/102 R |
| 3,852,032 | 12/1974 | Urbach ..................... 21/54 |
| 3,864,081 | 2/1975 | Logrippo ..................... 21/102 R |
| 3,894,236 | 7/1975 | Hazelrigg ..................... 250/435 |
| 3,920,650 * | 11/1975 | Spencer et al. ..................... 260/251.5 |
| 3,926,556 | 12/1975 | Boucher ..................... 21/54 R |
| 3,927,325 | 12/1975 | Hungate et al. ..................... 250/435 |
| 4,124,598 | 11/1978 | Hearst et al. ..................... 260/343.21 |
| 4,139,348 | 2/1979 | Swartz ..................... 23/232 E |
| 4,169,204 | 9/1979 | Hearst et al. ..................... 546/270 |
| 4,181,128 | 1/1980 | Swartz ..................... 128/207.21 |
| 4,196,281 | 4/1980 | Hearst et al. ..................... 536/28 |
| 4,312,883 | 1/1982 | Baccichetti et al. ..................... 424/279 |
| 4,321,918 | 3/1982 | Clark, II ..................... 128/124 R |
| 4,321,919 | 3/1982 | Edelson ..................... 128/124 R |
| 4,336,809 | 6/1982 | Clark ..................... 128/665 |
| 4,398,031 | 8/1983 | Bender et al. ..................... 549/282 |
| 4,398,906 | 8/1983 | Edelson ..................... 604/6 |
| 4,402,318 | 9/1983 | Edelson ..................... 604/6 |
| 4,407,282 | 10/1983 | Swartz ..................... 604/20 |
| 4,421,987 | 12/1983 | Herold ..................... 250/492.1 |
| 4,424,201 | 1/1984 | Valinsky et al. ..................... 424/3 |
| 4,428,744 | 1/1984 | Edelson ..................... 604/6 |
| 4,456,512 | 6/1984 | Bieler et al. ..................... 204/162 R |
| 4,464,166 | 8/1984 | Edelson ..................... 604/6 |
| 4,467,206 | 8/1984 | Taylor et al. ..................... 250/435 |
| 4,481,167 | 11/1984 | Ginter et al. ..................... 422/29 |
| 4,493,981 | 1/1985 | Payne ..................... 219/450 |
| 4,568,328 | 2/1986 | King ..................... 604/6 |
| 4,573,960 | 3/1986 | Goss ..................... 604/6 |
| 4,573,961 | 3/1986 | King ..................... 604/6 |
| 4,573,962 | 3/1986 | Troutner ..................... 604/6 |
| 4,576,143 | 3/1986 | Clark, III ..................... 128/1 R |
| 4,578,056 | 3/1986 | King et al. ..................... 604/6 |
| 4,596,547 | 6/1986 | Troutner ..................... 604/4 |
| 4,604,356 | 8/1986 | Blake, II ..................... 435/194 |
| 4,608,255 | 8/1986 | Kahn et al. ..................... 424/101 |
| 4,612,007 | 9/1986 | Edelson ..................... 604/5 |
| 4,613,322 | 9/1986 | Edelson ..................... 604/6 |
| 4,614,190 | 9/1986 | Stanco et al. ..................... 128/395 |
| 4,623,328 | 11/1986 | Hartranft ..................... 604/4 |
| 4,642,171 | 2/1987 | Sekine et al. ..................... 204/298 |
| 4,645,649 | 2/1987 | Nagao ..................... 422/186.3 |
| 4,648,992 | 3/1987 | Graf et al. ..................... 540/124 |
| 4,649,151 | 3/1987 | Dougherty et al. ..................... 514/410 |
| 4,651,739 | 3/1987 | Oseroff et al. ..................... 128/395 |
| 4,683,195 | 7/1987 | Mullis et al. ..................... 435/6 |
| 4,683,202 | 7/1987 | Mullis ..................... 435/91 |
| 4,683,889 | 8/1987 | Edelson ..................... 128/395 |
| 4,684,521 | 8/1987 | Edelson ..................... 424/101 |
| 4,693,981 | 9/1987 | Wiesehahn et al. ..................... 435/238 |
| 4,695,460 | 9/1987 | Holme ..................... 424/101 |
| 4,708,715 | 11/1987 | Troutner et al. ..................... 604/6 |
| 4,726,949 | 2/1988 | Miripol et al. ..................... 424/101 |

(List continued on next page.)

FOREIGN PATENT DOCUMENTS

| | | |
|---|---|---|
| 0 066886 | 6/1982 | (EP) . |
| 0 124 363 | 4/1984 | (EP) . |
| 0 196 515 A1 | 3/1986 | (EP) . |

(List continued on next page.)

OTHER PUBLICATIONS

Tyrakowska et al. J. Photochem. Photobiol. A : Chem 72: 235–241, Jan. 1993.*

(List continued on next page.)

Primary Examiner—Mukund J. Shah
Assistant Examiner—Hong Liu
(74) Attorney, Agent, or Firm—Greenlee Winner & Sullivan, P.C.

(57) ABSTRACT

Methods are provided for neutralization of microorganisms in fluids or on surfaces. Preferably the fluids contain blood or blood products and comprise biologically active proteins. Preferred methods include the steps of adding an activation-effective amount of a microorganism neutralizer with an isoalloxazine backbone to a fluid and exposing the fluid to a triggering event. Preferred triggering events include light of a suitable wavelength and intensity to activate the microorganism neutralizer or a pH sufficient to activate the microorganism neutralizer. Other fluids, including juices, water and the like, may also be decontaminated by these methods as may surfaces of foods, animal carcasses, wounds, food preparation surfaces and bathing and washing vessel surfaces. Compounds with an isoalloxazine backbone are also provided.

7 Claims, No Drawings

U.S. PATENT DOCUMENTS

| | | | |
|---|---|---|---|
| 4,727,027 | 2/1988 | Wiesehahn et al. | 435/173 |
| 4,737,140 | 4/1988 | Lee et al. | 604/4 |
| 4,748,120 | 5/1988 | Wiesehahn | 435/173 |
| 4,775,625 | 10/1988 | Sieber | 435/238 |
| 4,788,038 | 11/1988 | Matsunaga | 422/22 |
| 4,831,268 | 5/1989 | Fisch et al. | 250/432 R |
| 4,833,165 | 5/1989 | Louderback | 514/694 |
| 4,861,704 | 8/1989 | Reemtsma et al. | 435/1 |
| 4,866,282 | 9/1989 | Miripol et al. | 250/455.1 |
| 4,878,891 | 11/1989 | Judy et al. | 604/5 |
| 4,880,788 | 11/1989 | Moake et al. | 514/150 |
| 4,915,683 | 4/1990 | Alfano et al. | 128/665 |
| 4,921,473 | 5/1990 | Lee et al. | 494/27 |
| 4,930,516 | 6/1990 | Alfano et al. | 128/665 |
| 4,946,438 | 8/1990 | Reemtsma et al. | 604/53 |
| 4,948,980 | 8/1990 | Wedekamp | 250/504 R |
| 4,950,665 | 8/1990 | Floyd | 514/222.8 |
| 4,952,812 | 8/1990 | Miripol et al. | 250/455.1 |
| 4,960,408 | 10/1990 | Klainer et al. | 604/4 |
| 4,961,928 | 10/1990 | Holme et al. | 424/533 |
| 4,978,688 | 12/1990 | Louderback | 514/722 |
| 4,986,628 | 1/1991 | Lozhenko et al. | 350/96.29 |
| 4,992,363 | 2/1991 | Murphy | 435/2 |
| 4,994,367 | 2/1991 | Bode et al. | 435/2 |
| 4,998,931 | 3/1991 | Slichter et al. | 604/20 |
| 4,999,375 | 3/1991 | Bachynsky et al. | 514/455 |
| 5,011,695 | 4/1991 | Dichtelmuller et al. | 424/529 |
| 5,017,338 | 5/1991 | Surgenor | 422/41 |
| 5,020,995 | 6/1991 | Levy | 433/215 |
| 5,030,200 | 7/1991 | Judy et al. | 604/5 |
| 5,039,483 | 8/1991 | Sieber et al. | 422/28 |
| 5,041,078 | 8/1991 | Matthews et al. | 604/4 |
| 5,089,146 | 2/1992 | Carmen et al. | 210/782 |
| 5,089,384 | 2/1992 | Hale | 435/2 |
| 5,092,773 | 3/1992 | Levy | 433/224 |
| 5,095,115 * | 3/1992 | Grimmer et al. | 544/244 |
| 5,114,670 | 5/1992 | Duffey | 422/24 |
| 5,114,957 | 5/1992 | Hendler et al. | 514/356 |
| 5,120,649 | 6/1992 | Horowitz et al. | 435/713 |
| 5,123,902 | 6/1992 | Müller et al. | 604/21 |
| 5,133,932 | 7/1992 | Gunn et al. | 422/24 |
| 5,147,776 | 9/1992 | Koerner, Jr. | 435/2 |
| 5,150,705 | 9/1992 | Stinson | 128/396 |
| 5,166,528 | 11/1992 | Le Vay | 250/455.11 |
| 5,184,020 | 2/1993 | Hearst et al. | 250/455.11 |
| 5,185,532 | 2/1993 | Zabsky et al. | 250/455.11 |
| 5,192,264 | 3/1993 | Fossel | 604/4 |
| 5,216,251 | 6/1993 | Matschke | 250/455.11 |
| 5,229,081 | 7/1993 | Suda | 427/186 |
| 5,232,844 | 8/1993 | Horowitz et al. | 435/173.1 |
| 5,234,808 | 8/1993 | Murphy | 435/2 |
| 5,236,716 | 8/1993 | Carmen et al. | 424/532 |
| 5,247,178 | 9/1993 | Ury et al. | 250/438 |
| 5,248,506 | 9/1993 | Holme et al. | 424/533 |
| 5,258,124 | 11/1993 | Bolton et al. | 210/748 |
| 5,269,946 | 12/1993 | Goldhaber et al. | 210/767 |
| 5,273,713 | 12/1993 | Levy | 422/22 |
| 5,288,605 | 2/1994 | Lin et al. | 435/902 |
| 5,288,647 | 2/1994 | Zimlich, Jr. et al. | 436/174 |
| 5,290,221 | 3/1994 | Wolf, Jr. et al. | 604/4 |
| 5,300,019 | 4/1994 | Bischof et al. | 604/4 |
| 5,304,113 | 4/1994 | Sieber et al. | 604/4 |
| 5,318,023 | 6/1994 | Vari et al. | 128/633 |
| 5,340,716 | 8/1994 | Ullman et al. | 435/6 |
| 5,342,752 | 8/1994 | Platz et al. | 435/2 |
| 5,344,752 | 9/1994 | Murphy | 435/2 |
| 5,344,918 | 9/1994 | Dazey et al. | 530/381 |
| 5,358,844 | 10/1994 | Stossel et al. | 435/2 |
| 5,360,734 | 11/1994 | Chapman et al. | 435/238 |
| 5,366,440 | 11/1994 | Fossel | 604/4 |
| 5,376,524 | 12/1994 | Murphy et al. | 435/2 |
| 5,378,601 | 1/1995 | Gepner-Puszkin | 435/2 |
| 5,418,130 | 5/1995 | Platz et al. | 435/2 |
| 5,419,759 | 5/1995 | Naficyn | 604/5 |
| 5,427,695 | 6/1995 | Brown | 210/805 |
| 5,433,738 | 7/1995 | Stinson | 607/92 |
| 5,459,030 | 10/1995 | Lin et al. | 435/2 |
| 5,466,573 | 11/1995 | Murphy et al. | 435/2 |
| 5,474,891 | 12/1995 | Murphy | 435/2 |
| 5,482,828 | 1/1996 | Lin et al. | 435/2 |
| 5,487,971 | 1/1996 | Holme et al. | 435/2 |
| 5,503,721 | 4/1996 | Hearst et al. | 204/157.6 |
| 5,516,629 | 5/1996 | Park et al. | 435/2 |
| 5,527,704 | 6/1996 | Wolf, Jr. et al. | 435/283.1 |
| 5,536,238 | 7/1996 | Bischof | 604/6 |
| 5,545,516 | 8/1996 | Wagner | 435/2 |
| 5,547,635 | 8/1996 | Duthie, Jr. | 422/24 |
| 5,550,111 | 8/1996 | Suhadolnik et al. | 514/44 |
| 5,556,958 | 9/1996 | Carroll et al. | 536/25.3 |
| 5,556,993 | 9/1996 | Wollowitz et al. | 549/282 |
| 5,557,098 | 9/1996 | D'Silva | 250/222.1 |
| 5,569,579 | 10/1996 | Murphy | 435/2 |
| 5,571,666 | 11/1996 | Floyd et al. | 435/2 |
| 5,587,490 | 12/1996 | Goodrich, Jr. et al. | 549/282 |
| 5,593,823 | 1/1997 | Wollowitz et al. | 435/2 |
| 5,597,722 | 1/1997 | Chapman et al. | 435/238 |
| 5,607,924 | 3/1997 | Magda et al. | 514/44 |
| 5,622,867 | 4/1997 | Livesey et al. | 436/18 |
| 5,624,435 | 4/1997 | Furumoto et al. | 606/10 |
| 5,628,727 | 5/1997 | Hakky et al. | 604/6 |
| 5,639,376 | 6/1997 | Lee et al. | 210/645 |
| 5,639,382 | 6/1997 | Brown | 210/739 |
| 5,643,334 | 7/1997 | Eckhouse et al. | 607/88 |
| 5,652,096 | 7/1997 | Cimino | 435/6 |
| 5,653,887 | 8/1997 | Wahl et al. | 210/745 |
| 5,654,443 | 8/1997 | Wollowitz et al. | 549/282 |
| 5,658,530 | 8/1997 | Dunn | 422/24 |
| 5,658,722 | 8/1997 | Margolis-Nunno et al. | 435/2 |
| 5,683,661 | 11/1997 | Hearst et al. | 422/186.3 |
| 5,683,768 | 11/1997 | Shang et al. | 428/35.2 |
| 5,686,436 | 11/1997 | Van Dyke | 514/171 |
| 5,688,475 | 11/1997 | Duthie, Jr. | 422/186.3 |
| 5,691,132 | 11/1997 | Wollowitz et al. | 435/2 |
| 5,698,524 | 12/1997 | Mach et al. | 514/22 |
| 5,698,677 | 12/1997 | Eibl et al. | 530/381 |
| 5,702,684 | 12/1997 | McCoy et al. | 424/10.3 |
| 5,707,401 | 1/1998 | Talmore | 607/88 |
| 5,709,653 | 1/1998 | Leone | 604/20 |
| 5,709,991 | 1/1998 | Lin et al. | 435/2 |
| 5,712,086 | 1/1998 | Horowitz et al. | 435/2 |
| 5,714,328 | 2/1998 | Magda et al. | 435/6 |
| 5,739,013 | 4/1998 | Budowsky et al. | 435/91.1 |
| 5,756,553 | 5/1998 | Iguchi et al. | 514/772.3 |
| 5,772,960 | 6/1998 | Ito et al. | 422/41 |
| 5,789,150 | 8/1998 | Margolis-Nunno et al. | 435/2 |
| 5,789,601 | 8/1998 | Park et al. | 549/283 |
| 5,798,238 | 8/1998 | Goodrich, Jr. et al. | 435/173.3 |
| 5,798,523 | 8/1998 | Villenueve et al. | 250/234 |
| 5,817,519 | 10/1998 | Zelmanovic et al. | 436/63 |
| 5,827,644 | 10/1998 | Floyd et al. | 435/2 |
| 5,834,198 | 11/1998 | Famulok et al. | 435/6 |
| 5,843,459 | 12/1998 | Wang et al. | 424/231.1 |
| 5,846,961 | 12/1998 | Van Dyke | 514/171 |
| 5,854,967 | 12/1998 | Hearst et al. | 422/186.3 |
| 5,866,074 | 2/1999 | Chapman et al. | 422/82.09 |
| 5,869,701 | 2/1999 | Park et al. | 549/283 |
| 5,871,900 | 2/1999 | Wollowitz et al. | 435/2 |
| 5,876,676 | 3/1999 | Stossel et al. | 422/12 |
| 5,908,742 | 6/1999 | Lin et al. | 435/2 |
| 5,922,278 | 7/1999 | Chapman et al. | 422/22 |
| 5,935,092 | 8/1999 | Sun et al. | 604/4 |

| | | | |
|---|---|---|---|
| 5,976,884 | 11/1999 | Chapman et al. | 436/34 |
| 6,020,333 | 2/2000 | Berque | 514/251 |

FOREIGN PATENT DOCUMENTS

| | | |
|---|---|---|
| 0 491/757 | 9/1990 | (EP) . |
| 0 525 138 B1 | 12/1991 | (EP) . |
| 0 801 072 A2 | 10/1997 | (EP) . |
| 2674753 | 10/1992 | (FR) . |
| 2715303 | 7/1995 | (FR) . |
| 2718353 | 10/1995 | (FR) . |
| WO 89/06702 | 7/1989 | (WO) . |
| WO 91/02529 | 3/1991 | (WO) . |
| WO 92/11057 | 7/1992 | (WO) . |
| WO 92/17173 | 9/1992 | (WO) . |
| WO 94/07499 | 4/1994 | (WO) . |
| WO94/07426 | 4/1994 | (WO) . |
| WO 95/02325 | 1/1995 | (WO) . |
| WO95/11028 | 4/1995 | (WO) . |
| WO 95/12973 | 5/1995 | (WO) . |
| WO 95/16348 | 6/1995 | (WO) . |
| WO 96/14740 | 5/1996 | (WO) . |
| WO 97/07674 | 3/1997 | (WO) . |
| WO 97/22245 | 6/1997 | (WO) . |
| WO 97/36581 | 10/1997 | (WO) . |
| WO 97/36634 | 10/1997 | (WO) . |
| WO 98/30545 | 7/1998 | (WO) . |
| WO 98/31219 | 7/1998 | (WO) . |
| WO 99/11305 | 3/1999 | (WO) . |

OTHER PUBLICATIONS

Schoo et al. Macromolecules 25: 1633–1638, Jan. 1992.*

Herfeld et al. Anti–Ccancer drug Design 13: 337–359, 1998.*

CAS Printout for Herfeld et al., 1998.*

CAS Printout for Herfeld et al. Lab. Chim. Ther., Fac. Sci. Pharm. Biol. 5: 67–76, Jan. 1994.

Koziol et al., Bull. Pol. Acad. Sci. 39: 37–9, Jan. 1991.

U.S. application No. 09/119,666, Goodrich et al., filed Jul. 21, 1989.

U.S. application No. 09/357,188, Goodrich et al., filed Jul. 20,1999.

U.S. application No. 08/924,519, filed Sep. 5,1997.

Abdurashidova, G.G. et al., "Polynucleotide–protein itneractions in the translation system. Identification of proteins itneracting with tRNA in the A– and P–sites of *E. coli* ribosomes," (1979) *Nucleic Acids Res.* 6(12):3891–3909.

Brodie, A.F. and Watanabe, T., "Mode of action of vitamin K in microorganisms," (1966) *Vitam. Horm.* 24:447–463.

Budowsky, E.I. et al., "Induction of polynucleotide–protein cross–linkages by ultraviolet irradiation," (1986) *Eur. J. Biochem.* 159:95–101.

Budowsky, E.I. and Abdurashidova, G.G., "Polynucleotide–Protein Cross–Links Induced by Ultraviolet Light and Their Use for Structural Investigation of Nucleoproteins," (1989) *Progress in Nucleic Acid Res. and Mol. Biol.* 37:1–65.

Budowsky, E.I., "Problems and Prospects for Preparation of Killed Antiviral Vaccines," (1991) *Adv. Virus Res.* 39:255–290.

Budowsky, E.I. et al., "Principles of selective inactivation of viral genome. VI. Inactivation of the infectivity of the influenza virus by the action of β–propiolactone," (1991) *Vaccine* 9:398–402.

Budowsky, E.I. et al., "Principles of selective inactivation of viral genome. VII. Some peculiarities in determination of viral suspension infectivity during inactivation by chemical agents," (1991) *Vaccine* 9:473–476.

Budowsky, E.I. et al., "Principles of selective inactivation of viral genome. VIII. The influence of β–propiolactone on immunogenic and protective activities of influenza virus," (1993) *Vaccine* 11(3):343–348.

Budowsky, E.I. et al., "Preparation of cyclic 2',3'–monophosphates of oligoadenylates $(A2'p)_nA>p$ and $A3'p(A2'p)_{n-1}A>p$," (1994) *Eur. J. Biochem.* 220:97–104.

Cadet, J. et al., "Mechanisms and Products of Photosensitized Degradation of Nucleic Acids and Related Model Compounds," (1983) *Israel J. Chem.* 23:420–429.

Chow, C.S. and Barton, J.K., "Recognition of G–U mismatches by tris(4,7–diphenyl– 1,10–phenanthroline)rhodium(III)," (1992) *Biochemistry* 31(24):5423–5429.

Deutsch, E., "Vitamin K in medical practice: adults," (1966) *Vitam. Horm.* 24:665–680.

Ennever, J.F. and Speck, W.T., "Short Communication. Photochemical Reactions of Riboflavin: Covalent Binding to DNA and to Poly (dA)•Poly (dT)," (1983) *Pediatr. Res.* 17:234–236.

Goodrich, R.P. and Platz, M.S., "The design and development of selective, photoactivated drugs for sterilization of blood products," (1997) *Drugs of the Future* 22(2):159–171.

Hoffman, M.E. and Meneghini, R., "DNA Strand Breaks in Mammalian Cells Exposed to Light in the Presence of Riboflavin and Tryptophan," (1979) *Photochemistry and Photobiology* 29:299–303.

Ivanchenko, V.A. et al., "The photochemistry of purine components of nucleic acids. I. The efficiency of photolysis of adenine and guanine derivatives in aqueous solution," (1975) *Nucleic Acids Res.* 2(8):1365–1373.

Joshi, P.C., "Comparison of the DNA–damaging property of photosensitized riboflavin via singlet oxygen ($^1O_2$) and superoxide radical ($O_i$) mechanisms," (1985) *Toxicology Letters* 26:211–217.

Kabuta, H. et al. (1978), "Inactivation of viruses by dyes and visible light," Chem. Abstracts 87(1), Abstract No. 400626.

Kale, H. et al. (1992), "Assessment of the genotoxic potential of riboflavin and lumiflavin; B. Effect of light," Mutation Res. 298:17–23.

Klebanoff, M.A. et al., "The risk of childhood cancer after neonatal exposure to vitamin K," (1993) *New Eng.. J. Med.* 329(13):905–908.

Kobayashi et al. (1983), "The molecular mechanism of mutation. Photodynamic action of flavins on the RNA–synthesizing system," Chem. Abstracts 98(1), Abstract No. 1200.

Korycka–Dahl, M. and Richardson, T., "Photodegradation of DNA with fluorescent light in the presence of riboflavin, and photoprotection by flavin triplet–state quenchers," (1980) *Biochimica et Biophysica Acta* 610:229–234.

Kovalsky, O.I. and Budowsky, E.I., "Laser (Two–Quantum) Photolysis of Polynucleotides and Nucleoproteins: Quantitative Processing of Results," 1990, *Photochemistry and Photobiology* 5(6):659–665.

Kuratomi, K. and Kobayashi, Y., "Studies on the Interactions Between DNA and Flavins," (1977) *Biochemica et Biophysica Acta* 476:207–217.

Leontis, N.B. and Westhof, E., "The 5S rRNA loop E: chemical probing and phylogenetic data versus crystal structure," (1998) *RNA* 4:1134–1153.

Lim, A.C. and Barton, J.K., "Chemical probing of tDNA$^{Phe}$ with transition metal complexes: a structural comparison of RNA and DNA," (1993) *Biochemistry* 32:11029–11034.

Matthews, J.L. et al., "Photodynamic therapy of viral contaminants with potential for blood banking applications," (1988) *Transfusion* 28(1):81–83.

McCord, E.F., "Chemically induced dynamic nuclear polarization studies of yeast," (1984) *Biochemistry* 23:1935–1939.

Merenstein, G.B. et al. (Vitamin K Ad Hoc Task Force), "Controversies concerning vitamin K and the newborn," (1993) *Pediatrics* 91(5):1001–1003.

Naseem, I. et al., "Effect of alkylated and intercalated DNA on the generation of superoxide anion by riboflavin," (1988) *Bioscience Reports* 8(5):485–492.

North, J. et al. (1993), "New Trends in Photobiology (Invited Review)," J. Photochem. Photobiol. B: Biol. 17:99–108.

Peak, J.G. et al., "DNA Breakage Caused by 334–nm Ultraviolet Light is Enhanced by Naturally Occurring Nucleic Acid Components and Nucleotide Coenzymes," (1984) *Photochemistry and Photobiology* 39(5):713–716.

Piette, J. et al., "Alteration of Guanine Residues During Proflaving Mediated Photosensitization of DNA," (1981) *Photochemistry and Photobiology* 33:325–333.

Piette, J. et al., "Production of Breaks in Single– and Double–Stranded Forms of Bacteriophage φX174 DNA by Proflavine and Light Treatment," (1979) *Photochemistry and Photobiology* 30:369–378.

Pratt, R. et al., "Vitamin $K_5$ as an Antimicrobial Medicament and Preservative," (1950) *J. Am. Pharm. Ass'n* 39(3):127–134.

Product advertisement for "Ultracure 100SS Plus Specifications," EFOS USA, Inc., Williamsville, NY, USA.

Shwartzman, G., "Antibacterial Properties of 4–Amino–2–Methyl–1–Naphthol Hydrochloride," (1948) *Proc. Soc. Exp. Biol. Med.* 67:376–378.

Simukova, N.A. and Budowsky, E.I., "Conversion of Non-Covalent Interactions in Nucleoproteins into Covalent Bonds: UV–Induced Formation of Polynucleotide–Protein Crosslinks in Bacteriophage Sd Virions," (1974) *FEBS Letters* 38(3):299–303.

Spranger, J., "Does vitamin K cause cancer?" (1993) *Eur. J. Pediatr.* 152(2):174.

Speck, W.T. et al., "Further Observations on the Photooxidation of DNA in the Presence of Riboflavin," (1976) *Biochimica et Biphysica Acta* 435:39–44.

Tsugita, A. et al., "Photosensitized inactivation of ribonucleic acids in the presence of riboflavin," (1965) *Biochim. Biophys. Acta* 103:360–363.

Vest, M., "Vitamin K in medical practice: pediatrics," (1966) *Vitam. Horm.* 24:649–663.

Webb, R.B. and Malina, M.M., "Mutagenesis in *Escherichia coli* by Visible Light," (1967) *Science* 156:1104–1105.

Yang, H.Y. et al., "Vitamin $K_5$ as a Food Preservative," (1958) *Food Technology* 501– 504.

Maddox, J. (1991), "The working of vitamin K, " Nature 353(6346):695.

Merrifield, L.S. and Yang, H.Y. (1965), "Factors affecting the antimicrobial activity of vitamin K5, " Appl. Microbiol. 13(5):766–770.

Merrifield, L.S. and Yang, H.Y. (1965), "Vitamin K5 as a fungistatic agent, " Appl. Microbiol. 13(5):660–662.

Murata, A. et al. (1983), "Effect of vitamins other than vitamin C on viruses: virus–inactivating activity of vitamin K5, " J. Nutr. Sci. Vitaminol. (Tokyo) 29(6):721–724.

* cited by examiner

ISOALLOXAZINE DERIVATIVES TO NEUTRALIZE BIOLOGICAL CONTAMINANTS

BACKGROUND OF THE INVENTION

Contamination of blood supplies with infectious microorganisms such as HIV, hepatitis and other viruses and bacteria presents a serious health hazard for those who must receive transfusions of whole blood or administration of various blood components such as platelets, red cells, blood plasma, Factor VIII, plasminogen, fibronectin, antithrombin III, cryoprecipitate, human plasma protein fraction, albumin, immune serum globulin, prothrombin complex plasma growth hormones, and other components isolated from blood. Blood screening procedures currently available may miss contaminants. Thus, there is a need for sterilization procedures that effectively neutralize all infectious viruses and other microorganisms but do not damage cellular blood components, do not degrade desired biological activities of proteins, and preferably do not need to be removed prior to administration of the blood product to the patient.

The use of photosensitizers, compounds which absorb light of a defined wavelength and transfer the absorbed energy to an energy acceptor, has been proposed for blood component sterilization. Various photosensitizers have been proposed for use as blood additives. A review of some photosensitizers including psoralens, and some of the issues of importance in choosing photosensitizers for decontamination of blood products is provided in Goodrich, R. P., et al. (1997), "The Design and Development of Selective, Photoactivated Drugs for Sterilization of Blood Products," Drugs of the Future 22:159–171.

Some photosensitizers that have been proposed for use for blood component sterilization have undesirable properties. For example, European Patent Application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red and methylene blue, as blood additives. Another molecule, chlorpromazine, has been used as a photosensitizer; however its usefulness is limited by the fact that it should be removed from any fluid administered to a patient after the decontamination procedure because it has a sedative effect. Protoporphyrin, which occurs naturally within the body, can be metabolized to form a photosensitizer; however, its usefulness is limited in that it degrades the desired biological activities of proteins.

In addition to molecules which can serve as photosensitizers, alkylating agents have been proposed for use as blood contaminant neutralizers. Alkylating agents are believed to deactivate microorganisms by alkylating nucleophilic groups of amino acid residues and nucleic bases at a certain pH. Ethyleneimine has been reported to deactivate certain viruses (U.S. Pat. No. 5,891,075 (Budowsky, et al.),WO 97/07674 (published Mar. 6, 1997)).

U.S. patent application Ser. No. 09/119,666 and continuation in part Ser. No. 09/357,188, hereby incorporated by reference to the extent not inconsistent with the disclosure herein, describes methods and apparatus for neutralization of biological contaminants using endogenous photosensitizers, including 7,8-dimethyl-10-ribityl isoalloxazine (riboflavine).

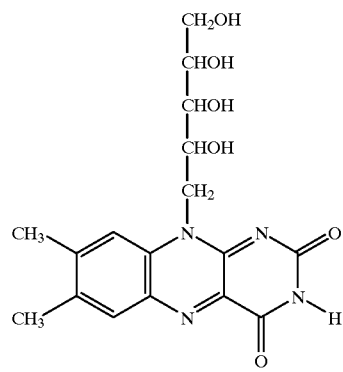

7,8-dimethyl-10-ribityl isoalloxazine 7,8-dimethyl-10-ribityl isoalloxazine (Riboflavine or vitamin B2) absorbs light from about 200 to 500 nm. The ring system core of 7,8-dimethyl-10-ribityl isoalloxazine is resistant to photodegradation but the ribityl side chain of riboflavin undergoes photodegradation. Photolysis of 7,8-dimethyl-10-ribityl isoalloxazine may form lumichrome (7,8-dimethylalloxazine) depending on conditions. 7,8-dimethylalloxazine strongly absorbs ultraviolet (UV) light and only weakly absorbs visible light.

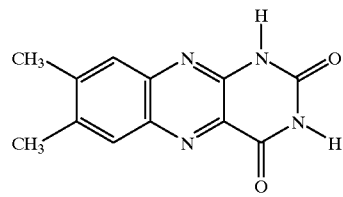

7,8-dimethylalloxazine

U.S. Pat. No. 5,811,144 discusses the treatment of beer with visible light under substantially anaerobic conditions to reportedly reduce the riboflavin content of the beer.

Small molecules such as those shown below which are derived from the ribityl side chain are expected to be products from the photolysis of riboflavin.

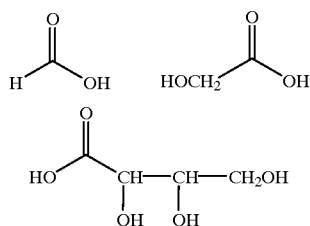

Incomplete photolysis of riboflavin leads to isoalloxazine-containing intermediates (Smith, E. C. and Metzler, D. E. (1963) J. Am. Chem. Soc. 85:3285–3288; Carins, W. L. and Metzler, D. E. (1971) J. Am. Chem. Soc. 93:2772–2777; Treadwell, G. E. et al. (1968) J. Chromatog. 35:376–388). Some of the identified compounds are:

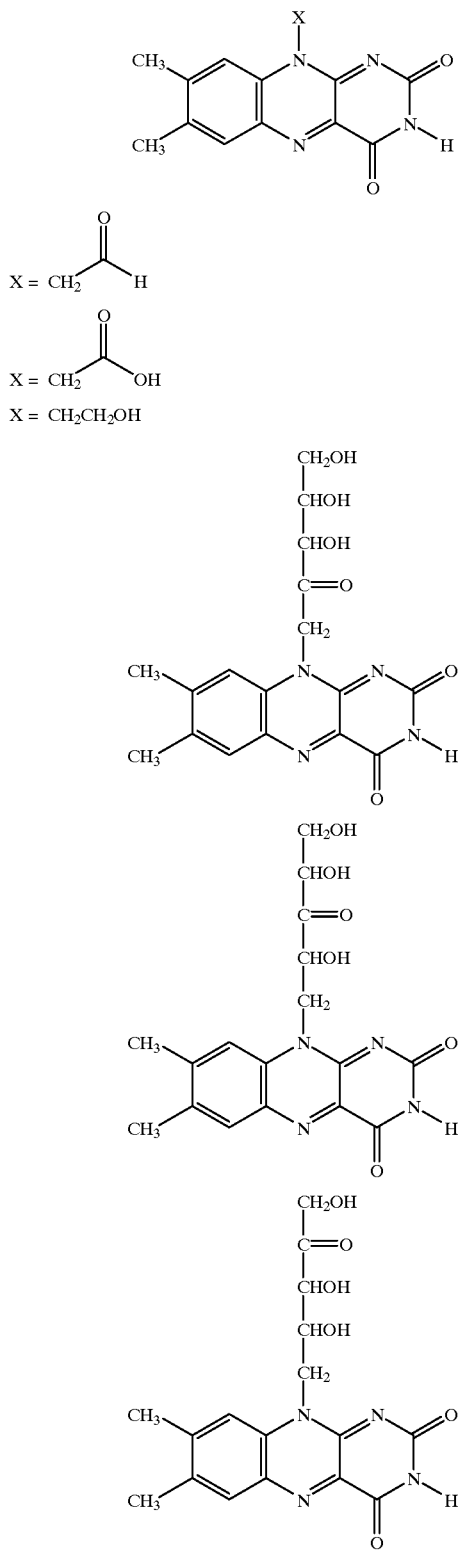

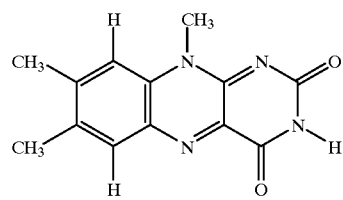

X = CH₂CHO
X = CH₂COOH
X = CH₂CH₂OH

These compounds absorb visible light and may convert to either lumichrome or another riboflavin metabolite, lumiflavin (7,8,10-trimethylisoalloxazine) upon complete photolysis, depending on the experimental conditions.

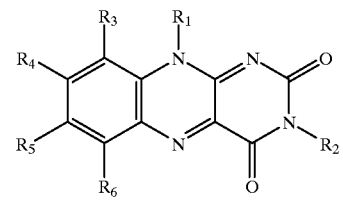

7,8,10-trimethylisoalloxazine

Lumichrome and lumiflavin are reported to be produced by the photolysis of milk (Parks, O. W. and Allen, C. (1977) Dairy Sci. 61:1038–1041; Toyosaki, T. and Hayashi, A. (1993) Milewissenschaft 48:607–609).

As a result of the degradation of 7,8-dimethyl-10-ribityl isoalloxazine upon exposure to light, a combination of visible and ultraviolet light is preferred in decontamination procedures using 7,8-dimethyl-10-ribityl isoalloxazine. Since UV light has a higher energy per photon than visible light, and because UV light is absorbed more strongly than visible light by useful compounds in the biological fluid, more damage to the useful components in the biological fluid containing the contaminants will occur when ultraviolet light is used in combination with visible light than when visible light can be used alone.

There is a need for compounds that neutralize microorganisms with visible light alone.

All publications referred to herein are hereby incorporated by reference to the extent not inconsistent with the disclosure herein.

BRIEF SUMMARY OF THE INVENTION

Methods are provided for treating a fluid or other material to neutralize at least some of the microorganisms and white cells which may be present therein or thereon. Such fluids may also contain one or more components selected from the group consisting of protein, e.g. biologically active protein such as a therapeutic protein, blood and blood constituents, without destroying the biological activity of such components. The methods comprise:

(a) mixing a neutralization-effective amount of a microorganism neutralizer of formula:

[structure showing isoalloxazine with substituents $R_1, R_2, R_3, R_4, R_5, R_6$]

with the fluid, wherein R1, R2, R3, R4, R5 and R6 are, independently from one another, selected from the group consisting of hydrogen, optionally substituted hydrocarbyl, alcohol, amine, polyamine, sulfate, phosphate, halogen selected from the group consisting of chlorine, bromine and iodine, salts of the foregoing, and —NR$^a$—(CR$^b$R$^c$)$_n$—X wherein X is a halogen selected from the group consisting of chlorine, bromine and iodine, R$^a$, R$^b$ and R$^c$ are, independently of each other, selected from the group consisting of hydrogen, optionally substituted hydrocarbyl, and halogen selected from the group consisting of chlorine, bromine and iodine, and n is an integer from 0 to 20;

provided that R1 is not —OH or a straight chain alkyl group where the second carbon of the chain is substituted with —OH or =O and R1, R4 and R5 are not all methyl groups when R2, R3 and R6 are all hydrogen;

(b) exposing the fluid to a triggering event, whereby at least some of the microorganisms are neutralized.

In one group of compounds, n is an integer between 0 and 5. In another group of compounds, n is an integer from

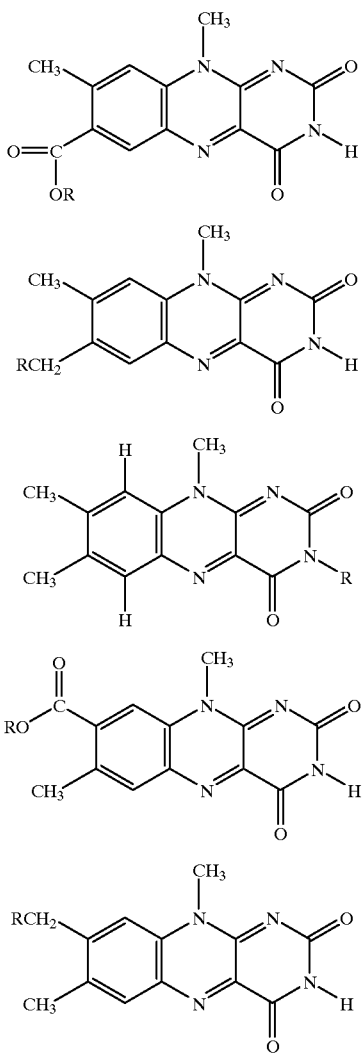

wherein R is a substituent imparting water solubility to the molecule, including, but not limited to, ascorbate, alcohol, polyalcohol; amine or polyamines, straight chain or cyclic saccharides, sulfates, phosphates, alkyl chains optionally substituted with —OH at any position, glycols, including polyethylene glycol and polyethers.

Another class of compounds of the invention include those wherein a R1, R2, R3, R4, R5 or R6 that is neither H nor CH$_3$ contains a halogen or is a halogen, wherein the halogen is selected from the group consisting of fluorine, chlorine, bromine and iodine. Particular embodiments of compounds of this class include compounds where a R1, R2, R3, R4, R5 or R6 that is neither H nor CH$_3$ is: —NR$^a$—(CR$^b$R$^c$)$_n$—X wherein X is a halogen selected from the group consisting of chlorine, bromine and iodine, or is a water soluble group, R$^a$, R$^b$ and R$^c$ are, independently of each other, selected from the group consisting of hydrogen and optionally substituted hydrocarbyl, and n is an integer from 0 to 20.

Preferred examples of compounds of this class are:

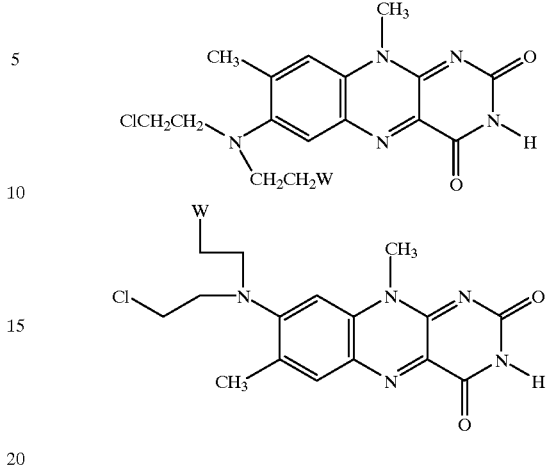

where W is a substituent imparting water solubility to the molecule, including, but not limited to, ascorbate, alcohol, polyalcohol; amine or polyamines, straight chain or cyclic saccharides, sulfates, phosphates, alkyl chains optionally substituted with —OH at any position, glycols, including polyethylene glycol and polyethers.

Another particular embodiment of compounds wherein a R1, R2, R3, R4, R5 or R6 that is neither H nor CH$_3$ contains a halogen or is a halogen includes compounds wherein a R1, R2, R3, R4, R5 or R6 that is neither H nor CH$_3$ is: X—(CH$_2$)$_n$—, wherein X is a halogen selected from the group consisting of chlorine, bromine and iodine, and n is an integer from 0 to 6. A preferred example of compounds of this class include:

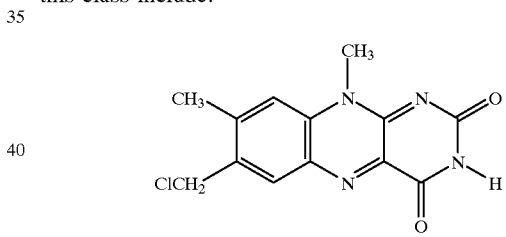

Other classes of compounds of this invention include those wherein R1 is CH$_2$—(CH$_2$OH)$_3$—CH$_2$OH and those wherein R1 is not CH$_2$—(CH$_2$OH)$_3$—CH$_2$OH. Also, those compounds wherein R3 and R6 are H are included in the invention.

Definitions

A "carbonyl compound" is any compound containing a carbonyl group (—C=O). The term "amine" refers to a primary, secondary, or tertiary amine group. A "polyamine" is a group that contains more than one amine group. A "sulfate" group is a salt of sulfuric acid. Sulfate groups include the group (SO$_4$)$^{2-}$. "Phosphates" contain the group PO$_4^{3-}$. "Glycols" are groups that have two alcohol groups per molecule of the compound. "Glycols" are also known as diols. A glycol is described by the formula: C$_n$H$_{2n}$(OH)$_2$, where n is an integer. An "aldehyde" is a group containing the formula —(C=O)—H. A "ketone" is a group with formula R—(C=O)—R, where R is not hydrogen. The R groups on ketones do not need to be the same. A "carboxylic acid" is a group which includes the formula: —COOH. An "ether" is a group containing —O—. A "salt" is a group where a hydrogen atom of an acid has been replaced with a metal atom or a positive radical, such as $NH_4^+$. "Ascorbate" includes groups with formula:

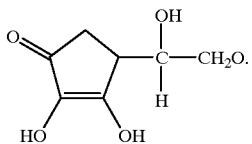

The term "hydrocarbyl" is used herein to refer generally to organic groups comprised of carbon chains to which hydrogen and optionally other elements are attached. $CH_2$ or CH groups and C atoms of the carbon chains of the hydrocarbyl may be replaced with one or more heteroatoms (i.e., non-carbon atoms). Suitable heteroatoms include but are not limited to O, S, P and N atoms. The term hydrocarbyl includes, but is not limited to alkyl, alkenyl, alkynyl, ether, polyether, thioether, straight chain or cyclic saccharides, ascorbate, aminoalkyl, hydroxylalkyl, thioalkyl, aryl and heterocyclic aryl groups, optionally substituted isoalloxazine molecules, amino acid, polyalcohol, glycol, groups which have a mixture of saturated and unsaturated bonds, carbocyclic rings and combinations of such groups. The term also includes straight-chain, branched-chain and cyclic structures or combinations thereof. Hydrocarbyl groups are optionally substituted. Hydrocarbyl substitution includes substitution at one or more carbons in the group by moieties containing heteroatoms. Suitable substituents for hydrocarbyl groups include but are not limited to halogens, including chlorine, fluorine, bromine and iodine, OH, SH, $NH_2$, COH, $CO_2H$, $OR_a$, $SR_a$, $NR_aR_b$, $CONR_aR_b$, where $R_a$ and $R_b$ independently are alkyl, unsaturated alkyl or aryl groups.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups are $C_{1-C_6}$ alkyl and include among others methyl, ethyl, n-propyl, and isopropyl groups.

The term "cycloalkyl" refers to alkyl groups having a hydrocarbon ring, particularly to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

Aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitation: vinyl, allyl, propenyl, isopropenyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, COH, $CO_2H$, $OR_c$, $SR_c$, P, PO, $NR_cR_d$, $CONR_cR_d$, and halogens, particularly chlorines and bromines where $R_c$ and $R_d$, independently, are alkyl, unsaturated alkyl or aryl groups. Preferred alkyl and unsaturated alkyl groups are the lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl (—$C_6H_5$), or naphthyl (—$C_{10}H_7$). Suitable substituents for aryl groups include among others, alkyl groups, unsaturated alkyl groups, halogens, OH, SH, $NH_2$, COH, $CO_2H$, $OR_e$, $SR_e$, $NR_eR_f$, $CONR_eR_f$, where $R_e$ and $R_f$ independently are alkyl, unsaturated alkyl or aryl groups. Preferred substituents are OH, SH, $OR_e$, and $SR_e$ where $R_e$ is a lower alkyl, i.e., an alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as —$CO_2$—, —CO—, —O—, —S—, —P—, —NH—, —CH=CH— and —$(CH_2)_l$— where l is an integer from 1 to about 5, and particularly —$CH_2$—. Examples of aryl groups having bridging substituents include phenylbenzoate. Substituents also include moieties, such as —$(CH_2)_1$—, —O—$(CH_2)_l$— or —OCO—$(CH_2)_l$—, where l is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substituents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethyl propoxy, 1,1 -dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethyl propoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Amino acids" as used herein include naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, o-, m-, and p-tyrosine, tryptophan, glutamine, asparagine, proline and hydroxyproline. "Amino acid" as used herein includes amino acid residues and amino acid side chains. An "amino acid residue" is an amino acid radical —NHCH(R)C(O)—, wherein R is an amino acid side chain, except for the amino acid residues of proline and hydroxyproline which are —N($CH_2$—$CH_2$—$CH_2$)CHC(O)— and —N(CH—CHOH$CH_2$)CHC(O)—, respectively. An amino acid side chain is a radical found on the α-carbon of an α-amino acid as defined herein, where the radical is either hydrogen (side chain of glycine), methyl (side chain of alanine), or is a radical bonded to the α-carbon by a methylene (—$CH_2$—), or phenyl group.

A protected glucose derivative takes its usual meaning in the art and includes a glucose molecule wherein some of the hydroxyl groups are substituted with acetate groups.

"Contacting" reaction components with each other refers to providing a medium and/or reaction chamber in which the reaction components are placed together so that they can react with each other. Preferably, the reaction components are suspended or dissolved in a carrier fluid which is a liquid medium. "Maintaining reaction components in contact" means keeping the components together in such a way that they can react with each other.

"Straight chain or cyclic saccharides" include mono-, di- and poly-, straight chain and cyclic saccharides that are optionally substituted with an amino group which is optionally acetylated. Straight chain saccharides that are useful in this invention include but are not limited to those molecules with a chain of 5 or 6 carbon atoms with one or more —OH groups attached, and either an aldehyde or ketone group. Cyclic saccharides are saccharides that are in a ring form. Disaccharides are compounds wherein two monosaccharide groups are linked. Polysaccharides are compounds wherein more than two monosaccharide groups are linked. Specific examples of saccharides useful in this invention include glucose, ribose and glucosamine, among others.

"Isoalloxazine", "isoalloxazine derivative" or "core structure of isoalloxazine" include compounds that comprise the structure:

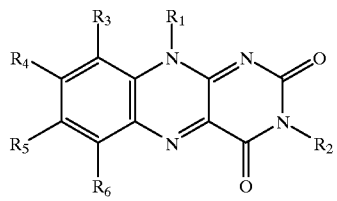

where R1–R6 are substituted with various substituents, as described elsewhere.

As used herein, the term "neutralization of a microorganism" or "neutralizing" means totally or partially preventing the microorganism from replicating, either by killing the microorganism or otherwise interfering with its ability to reproduce. A "neutralizer" is a compound that is capable of neutralizing a microorganism. The neutralizers useful in this invention include molecules with the core structure of isoalloxazine, as defined above. To "activate the microorganism neutralizer" is to expose the microorganism neutralizer to a triggering event that causes it to become active toward neutralizing microorganisms.

Microorganisms include viruses (both extracellular and intracellular), bacteria, bacteriophages, fungi, blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include $\Phi$X174, $\Phi$6, $\lambda$, R17, $T_4$, and $T_2$. Exemplary bacteria include *P. aeruginosa, S. aureus, S. epidermis, L. monocytogenes, E. coli, K. pneumonia* and *S. marcescens*. Neutralization of white blood cells may be desirable when suppression of immune or autoimmune response is desired, e.g., in processes involving transfusion of red cells, platelets or plasma when donor white blood cells may be present.

"Triggering event" refers to the stimulus that activates the microorganism neutralizer. Preferred triggering events include exposure of the neutralizer to an neutralization effective wavelength of light, or a pH sufficient to activate the neutralizer to neutralize microorganisms.

"Water soluble group" includes a group that, when included as a substituent on the neutralizer, imparts substantial solubility in water to the compound. Typically, the compound is soluble in water at a concentration of about 10–150 $\mu$M. Water soluble groups as referred to in this invention include, but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers.

The term "biologically active" means capable of effecting a change in a living organism or component thereof. "Biologically active" with respect to "biologically active protein" as referred to herein does not refer to proteins which are part of the microorganisms being neutralized. Similarly, "non-toxic" with respect to the neutralizers means low or no toxicity to humans and other mammals, and does not mean non-toxic to the microorganisms being neutralized. "Substantial destruction" of biological activity means at least as much destruction as is caused by porphyrin and porphyrin derivatives, metabolites and precursors which are known to have a damaging effect on biologically active proteins and cells of humans and mammals. Similarly, "substantially non-toxic" means less toxic than porphyrin, porphyrin derivatives, metabolites and precursors that are known for blood sterilization. Preferably, neutralizers are less toxic than porphyrin, porphyrin derivatives, metabolites and precursors that are known for blood sterilization.

The term "blood product" as used herein includes blood constituents and therapeutic protein compositions containing proteins derived from blood as defined above. Fluids containing biologically active proteins other than those derived from blood may also be treated by the methods of this invention. Such fluids may also contain one or more components selected from the group consisting of protein, e.g. biologically active protein such as a therapeutic protein, blood and blood constituents, without destroying the biological activity of such components.

Decontamination methods of this invention using isoalloxazine derivatives as defined above do not substantially destroy the biological activity of fluid components other than microorganisms. As much biological activity of these components as possible is retained, although in certain instances, when the methods are optimized, some loss of biological activity, e.g., denaturization of protein components, must be balanced against effective decontamination of the fluid. So long as fluid components retain sufficient biological activity to be useful for their intended or natural purposes, their biological activities are not considered to be substantially destroyed.

"Decomposition" of the neutralizer upon exposure to light refers to the chemical transformation of the neutralizer into new compounds. An example of decomposition of the neutralizer is the production of lumichrome upon exposure of riboflavin to visible light.

A "photosensitizer" is defined as any compound which absorbs radiation of one or more defined wavelengths and subsequently utilizes the absorbed energy to carry out a chemical process. Photosensitizers of this invention may include compounds which preferentially adsorb to nucleic acids, thus focusing their photodynamic effect upon microorganisms and viruses with little or no effect upon accompanying cells or proteins. Other photosensitizers of this invention are also useful, such as those using singlet oxygen-dependent mechanisms.

An "alkylating agent" is a compound that reacts with amino acid residues and nucleic bases and inhibits replication of microorganisms.

DETAILED DESCRIPTION OF THE INVENTION

The contaminant neutralizers of the invention neutralize microorganisms by exposure to a triggering event, preferably by exposure to an activation-effective wavelength of light in the uv/visible region of the spectrum or an activation-effective pH. The neutralizer must be one which does not substantially destroy desired components of the fluid being decontaminated, and also preferably which does not degrade into products which substantially destroy desired components or have significant toxicity or substantially decompose into ultraviolet light absorbing compounds.

In embodiments of the invention using light as a triggering event, the fluid containing an appropriate concentration of the neutralizer is exposed to photoradiation of the appropriate wavelength to activate the neutralizer, using an amount of photoradiation sufficient to activate the neutralizer, but less than that which would cause substantial damage to the biological components or substantially interfere with biological activity of other proteins present in the fluid. The wavelength of light used and the amount of radiation used will depend on the neutralizer selected, as is known to the art or readily determinable without undue experimentation by one of ordinary skill in the art, using literature sources or direct undue experimentation by one of ordinary skill in the art, using literature sources or direct measurement. Preferably the light source is a uv/visible light source providing 320 nm to about 700 nm, and more preferably about 365 nm to about 650 nm of radiation. The amount of neutralizer to be mixed with the fluid will be an amount sufficient to adequately neutralize microorganisms therein. Preferably the neutralizer is soluble in the fluid and present in an amount less than the upper solubility limit of the neutralizer in the fluid. As taught herein, optimal concentrations for desired neutralizers may be readily determined by those skilled in the art without undue experimentation. Preferably, the smallest efficacious concentration of neutralizer is used. Typically, the neutralizer is used in a concentration of at least about 1 $\mu$M up to the solubility of the neutralizer in the fluid, and typically the concentration of neutralizer is about 10 $\mu$M. Other concentrations are also able to be used. An excess of neutralizer may be present in the solution. The neutralizer may also be used in a suspension, where the neutralizer is not soluble in the fluid, provided that adequate mixing is provided to contact the neutralizer with the fluid. The neutralizer may also be removed from the fluid prior to administration of the fluid to a patient. All other parameters that may be involved in a decontamination system, including appropriate temperatures for the reaction of the neutralizer as well as the ranges of temperature, photoradiation intensity and duration, and neutralizer concentration which will optimize microbial neutralization and minimize damage to desired proteins and/or cellular components in the fluid are also easily determined as is known in the art or readily determinable without undue experimentation by one of ordinary skill in the art, using literature sources or direct measurement.

In embodiments of this invention using pH to neutralize the contaminants, the appropriate pH, concentration of neutralizer that is effective, and other parameters are determined by means known to one of ordinary skill in the art. In particular embodiments, contacting the contaminant neutralizer with the fluid containing microorganisms to be neutralized may be sufficient to activate the contaminant neutralizer (i.e., the triggering event when pH is used to activate the microorganism neutralizer may not need to be externally applied). An effective concentration is generally from about 10–100 $\mu$M. A pH of about 5 to about 8 is generally effective to activate the neutralizer. Other concentrations and pH's may be used.

A solution or suspension of contaminant neutralizer may be prepared and stored and when desired, used by contacting with fluid or other substance containing contaminants and exposing to a triggering event.

Once such system requirements have been determined, the appropriate apparatus may be designed. Batch or flow-through systems may be used, for example. The isoalloxazine derivatives of this invention can be used in the decontamination systems described in U.S. Pat. Nos. 5,290,221, 5,536,238, 5,290,221 and 5,536,238, and U.S. patent application Ser. Nos. 09/119,666 and 09/357,188. In general, the fluid to be decontaminated is mixed with neutralizer. If light is used to neutralize the contaminants, the fluid and neutralizer are irradiated with a sufficient amount of photoradiation at an appropriate wavelength to activate the neutralizer to react with microorganisms in the fluid such that microorganisms in the fluid are neutralized. If pH is used to neutralize the contaminants, the pH of the fluid and neutralizer is changed, if necessary, by any means known in the art.

Examples of materials which may be treated by the methods of this invention are whole blood and aqueous compositions containing biologically active proteins derived from blood or blood constituents. Packed red cells, platelets and plasma (fresh or fresh frozen plasma) are exemplary of such blood constituents. In addition, therapeutic protein compositions containing proteins derived from blood, such as fluids containing biologically active protein useful in the treatment of medical disorders, e.g., factor VIII, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen streptokinase complex, ceruloplasmin, transferrin, haptoglobin, antitrypsin and prekallikrein may be treated by the decontamination methods of this invention. Other fluids which could benefit from the treatment of this invention are peritoneal solutions used for peritoneal dialysis which are sometimes contaminated during connection, leading to peritoneal infections.

This method is also useful for treating other fluids including fluids which are meant for nourishment of humans or animals such as water, fruit, juices, milk, broths, soups and the like. The method is also useful for treating parenteral solutions. This invention may also be used to treat surfaces, as described in U.S. patent application Ser. No. 09/119,666. The isoalloxazine derivative compounds of this invention may also coat surfaces such as blood or peritoneal dialysis tubing sets to assure sterile connections and sterile docking.

The neutralizer may be applied in a suitable carrier such as water or a solution containing other treatment additives, by spraying, dipping, wiping on, or by other means known to the art. The amount of neutralizer and the conditions to activate the neutralizer required for treatment will be readily determined by one of skill in the art without undue experimentation depending on the level of contamination and the material being treated.

The activated neutralizer is capable of neutralizing the microorganisms present, such as by interfering to prevent their replication. This may occur with activation of the molecule with uv/visible light, or may occur by the nature of the substituent on the isoalloxazine core and an alteration of the pH of the system in the absence of light. Specificity of action of the neutralizer may be conferred by the close proximity of the neutralizer to the nucleic acid of the microorganism and this may result from binding of the neutralizer to the nucleic acid. "Nucleic acid" includes ribonucleic acid (RNA) and deoxyribonucleic acid (DNA). Other Neutralizers may act by binding to cell membranes or by other mechanisms. The neutralizer may also be targeted to the microorganism to be neutralized by covalently coupling to an antibody, preferably a specific monoclonal antibody to the microorganism.

Enhancers may also be added to the fluid to make the process more efficient and selective. Such enhancers include antioxidants or other agents to prevent damage to desired fluid components or to improve the rate of neutralization of microorganisms and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, trolox, glycerol, and mixtures thereof The use of the compounds of this invention to neutralize microorganisms requires mixing or contacting the isoalloxazine derivative with the material to be decontaminated. Mixing or contacting may be done by simply adding the neutralizer or a solution containing the neutralizer to a fluid to be decontaminated. In one embodiment using light to neutralize the microorganisms, the material to be decontaminated to which a light-triggered neutralizer has been added is flowed past a photoradiation source, and the flow of the material generally provides sufficient turbulence to distribute the neutralizer throughout the fluid to be decontaminated. In another embodiment, the fluid and light-triggered neutralizer are placed in a photopermeable container and irradiated in batch mode, preferably while agitating the container to fully distribute the photosensitizer and expose all the fluid to the radiation. In another embodiment, insoluble materials may be used in the process of this invention, for example, by suspending the isoalloxazine derivative in the biological fluid and exposing the fluid and isoalloxazine derivative to the triggering event. In another embodiment, the pH-triggered compound is placed in contact with the fluid to be treated. In some embodiments using a pH-triggered compound, the pH of the fluid-compound mixture will require changing in order to trigger neutralization by means known to one of ordinary skill in the art, such as the use of acid or base.

The fluid containing the photosensitizer may be flowed into a photopermeable container for irradiation. The term "container" refers to a closed or open space, which may be made of rigid or flexible material, e.g., may be a bag or box or trough. It may be closed or open at the top and may have openings at both ends, e.g., may be a tube or tubing, to allow for flow-through of fluid therein. A cuvette has been used to exemplify one embodiment of the invention involving a flow-through system. Collection bags, such as those used with the Trima™ Spectra™ and apheresis systems of Cobe Laboratories, Inc., have been used to exemplify another embodiment involving batch-wise treatment of the fluid.

The term "photopermeable" means the material of the container is adequately transparent to photoradiation of the proper wavelength for activating the photosensitizer. In the flow-through system, the container has a depth (dimension measured in the direction of the radiation from the photoradiation source) sufficient to allow photoradiation to adequately penetrate the container to contact photosenisitizer molecules at all distances from the light source and ensure inactivation of microorganisms in the fluid to be decontaminated, and a length (dimension in the direction of fluid flow) sufficient to ensure a sufficient exposure time of the fluid to the photoradiation. The materials for making such containers, depths and lengths of containers may be easily determined by those skilled in the art without undue experimentation following the teachings hereof, and together with the flow rate of fluid through the container, the intensity of the photoradiation and the absorptivities of the fluid components, e.g., plasma, platelets, red blood cells, will determine the amount of time the fluid needs to be exposed to photoradiation. For 7,8-dimethyl-10-ribityl isoalloxazine, a preferred amount of radiation is between about 1J/cm$^2$ to 120J/cm$^2$.

In another embodiment involving batch-wise treatment, the fluid to be treated is placed in a photopermeable container which is agitated and exposed to photoradiation for a time sufficient to substantially inactivate the microorganisms. The photopermeable container is preferably a blood bag made of transparent or semitransparent plastic, and the agitating means is preferably a shaker table. The photosensitizer may be added to the container in powdered or liquid form and the container agitated to mix the photosensitizer with the fluid and to adequately expose all the fluid to the photoradiation to ensure inactivation of microorganisms.

Photosensitizer may be added to or flowed into the photopermeable container separately from the fluid being treated or may be added to the fluid prior to placing the fluid in the container. In one embodiment, photosensitizer is added to anticoagulant and the mixture of photosensitizer and anticoagulant are added to the fluid.

In decontamination systems of this invention, the photoradiation source may be connected to the photopermeable container for the fluid by means of a light guide such as a light channel or fiber optic tube which prevents scattering of the light between the source and the container for the fluid, and more importantly, prevents substantial heating of the fluid within the container. Direct exposure to the light source may raise temperatures as much as 10 to 15° C., especially when the amount of fluid exposed to the light is small, which can cause denaturization of blood components. Use of the light guide keeps any heating to less than about 2° C. The method may also include the use of temperature sensors and cooling mechanisms where necessary to keep the temperature below temperatures at which desired proteins in the fluid are damaged. Preferably, the temperature is kept between about 0° C. and about 45° C., more preferably between about 4° C. and about 37° C., and most preferably about 22° C.

Any means for adding the photosensitizer to the fluid to be decontaminated and for placing the fluid in the photopermeable container known to the art may be used, such means typically including flow conduits, ports, reservoirs, valves, and the like. Preferably, the system includes means such as pumps or adjustable valves for controlling the flow of the photosensitizer into the fluid to be decontaminated so that its concentration may be controlled at effective levels as described above. In one embodiment, photosensitizer is mixed with the anticoagulant feed to a blood apheresis system. For endogenous photosensitizers and derivatives having sugar moieties, the pH of the solution is preferably kept low enough, as is known to the art, to prevent detachment of the sugar moiety. Preferably the photosensitizer is added to the fluid to be decontaminated in a pre-mixed aqueous solution, e.g., in water or storage buffer solution.

The photopermeable container for the flow-through system may be a transparent cuvette made of polycarbonate, glass, quartz, polystyrene, polyvinyl chloride, polyolefin, or other transparent material. The cuvette may be enclosed in a radiation chamber having mirrored walls. A photoradiation enhancer such as a second photoradiation source or reflective surface may be placed adjacent to the cuvette to increase the amount of photoradiation contacting the fluid within the cuvette. The system preferably includes a pump for adjusting the flow rate of the fluid to desired levels to ensure substantial decontamination as described above. The cuvette has a length, coordinated with the flow rate therethrough, sufficient to expose fluid therein to sufficient photoradiation to effect substantial decontamination thereof.

Also preferably the cuvette is spaced apart from the light source a sufficient distance that heating of the fluid in the cuvette does not occur, and light is transmitted from the light source to the cuvette by means of a light guide.

In another embodiment the fluid is placed in a photopermeable container such as a blood bag, e.g. used with the apheresis system described in U.S. Pat. No. 5,653,887, and agitated while exposing to photoradiation. Suitable bags include collection bags as described herein. Collection bags used in the Spectra™ system or Trima™ apheresis system of Cobe Laboratories, Inc. are especially suitable. Shaker tables are known to the art, e.g. as described in U.S. Pat. No. 4,880,788. The bag is equipped with at least one port for adding fluid thereto. In one embodiment the photosensitizer, preferably 7,8-dimethyl-10-ribityl-isoalloxazine, is added to the fluid-filled bag in powder form. The bag is then placed on a shaker table and agitated under photoradiation until substantially all the fluid has been exposed to the photoradiation. Alternatively, the bag may be prepackaged with the powdered photosensitizer contained therein. The fluid to be decontaminated may then be added through the appropriate port.

Decontamination systems as described above may be designed as stand-alone units or may be easily incorporated into existing apparatuses known to the art for separating or treating blood being withdrawn from or administered to a patient. For example, such blood-handling apparatuses include the COBE Spectra™ or TRIMA® apheresis systems, available from Cobe Laboratories, Inc., Lakewood, Colo., or the apparatuses described in U.S. Pat. No. 5,653,887 and U.S. Ser. No. 08/924,519 filed Sep. 5, 1997 (PCT Publication No. WO 99/11305) of Cobe Laboratories, Inc. as well as the apheresis systems of other manufacturers. The decontamination system may be inserted just downstream of the point where blood is withdrawn from a patient or donor, just prior to insertion of blood product into a patient, or at any point before or after separation of blood constituents. The photosensitizer is added to blood components along with anticoagulant in a preferred embodiment, and separate irradiation sources and cuvettes are placed downstream from collection points for platelets, for plasma and for red blood cells. The use of three separate blood decontamination systems is preferred to placement of a single blood decontamination system upstream of the blood separation vessel of an apheresis system because the lower flow rates in the separate component lines allows greater ease of irradiation. In other embodiments, decontamination systems of this invention may be used to process previously collected and stored blood products.

When red blood cells are present in the fluid being treated, as will be appreciated by those skilled in the art, to compensate for absorption of light by the cells, the fluid may be thinned, exposed to higher energies of radiation for longer periods, agitated for longer periods or presented to photoradiation in shallower containers or conduits than necessary for use with other blood components.

The wavelength at which the photosensitizer is activated is determined as described herein, using literature sources or direct measurement. Its solubility in the fluid to be decontaminated or in a combination of carrier fluid and fluid to be contaminated is also so determined. The ability of photoradiation at the activating wavelength to penetrate the fluid to be decontaminated must also be determined as taught herein. Appropriate temperatures for the reaction of the photosensitizer with its substrate are determined, as well as the ranges of temperature, photoradiation intensity and duration, and photosensitizer concentration which will optimize microbial inactivation and minimize damage to desired proteins and/or cellular components in the fluid.

Once such system requirements have been determined for flow-through systems, apparatuses may be designed which provide the correct flow rates, photopermeabilities, and light intensities to cause inactivation of microorganisms present in the fluid, as is taught herein. The fluid to be decontaminated is mixed with photosensitizer and then irradiated with a sufficient amount of photoradiation to activate the photosensitizer to react with microorganisms in the fluid such that microorganisms in the fluid are inactivated. The amount of photoradiation reaching microorganisms in the fluid is controlled by selecting an appropriate photoradiation source, an appropriate distance of the photoradiation source from the fluid to be decontaminated, which may be increased through the use of light guides to carry the photoradiation directly to the container for the fluid, an appropriate photopermeable material for the container for the fluid, an appropriate depth to allow full penetration of the photoradiation into the container, photoradiation enhancers such as one or more additional photoradiation sources, preferably on the opposite side of the container from the first, or reflectors to reflect light from the radiation source back into the container, appropriate flow rates for the fluid in the container and an appropriate container length to allow sufficient time for inactivation of microorganisms present. Temperature monitors and controllers may also be required to keep the fluid at optimal temperature.

EXAMPLES

Example 1

Absorbance Profile of Isoalloxazine Derivative

A sample of an isoalloxazine derivative is analyzed using a scanning UV spectrophotometer over the region 200 to 900 nm. For analysis, the sample is dissolved in distilled water. An absorption spectrum is obtained, and extinction coefficients at the absorbance maxima and other wavelengths of interest are determined. From the absorption spectrum and extinction coefficients, appropriate wavelengths for irradiation are determined. An appropriate wavelength is one at which the extinction coefficient is sufficient to ensure adequate activation of the sensitizer in solution.

Example 2

Neutralization of Microorganisms with Isoalloxazine Derivatives Using Light 7, 8, 10-trimethyl, 3-sulfonyl isoalloxazine is dissolved in blood at a concentration of 10 $\mu$M. The sample is spiked with a representative microorganism. Flow of the sample through an irradiation chamber is maintained and the sample is irradiated with a neutralization-effective level of light at a wavelength determined to be appropriate for neutralization, as described above. The extent of neutralization of the microorganism is measured by methods known in the art.

Example 3 pH Sensitivity Studies 7-chloroethylamino-8,10-methyl isoalloxazine is dissolved in blood at concentrations of 10–100 $\mu$M. The solutions are spiked with a representative microorganism. Aliquots are removed and the pH of different aliquots is adjusted to 1.0, 3.0, 5.0, 7.0, 9.0 with sodium carbonates. The solutions are mixed to distribute the components. The neutralization results are determined as described above.

Synthesis

Carboxyriboflavin (1, McCormick, D. (1970) J. Heter. Chem. 7:447) is photolyzed in aqueous alkali to form a carboxylumiflavine (2).

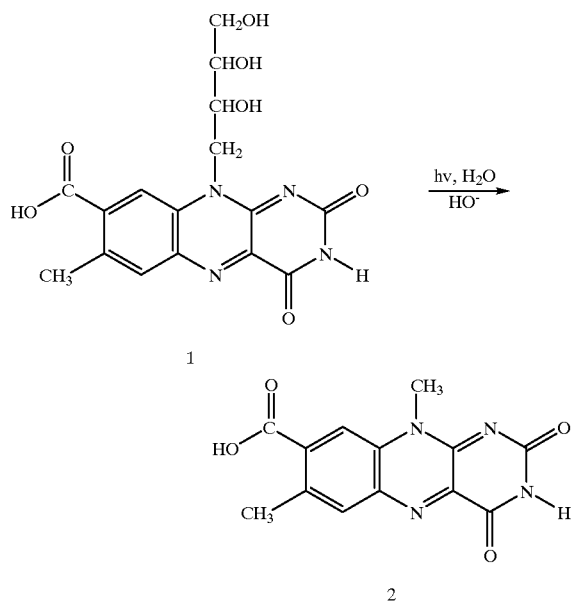

Compound 2 is converted to an acid chloride 3 with oxallylchloride.

Lumiflavine amine 5 is converted into compound 6 by the procedure of J. L. Everett, et al. (1953) J. Chem. Soc., p 2386.

Compound 3 is reacted with ascorbate ion, glucosamine, a protected glucose derivative or di or triethylene glycol to form a water soluble derivative 4 where the light sensitive water soluble moiety W is far removed from the amide containing ring.

Compound 3 is reacted with sodium azide in acetone to effect a Curtius Rearrangement. This forms compound 5, upon work-up. This reaction effectively replaces a $CO_2H$ group with an $NH_2$ group.

-continued

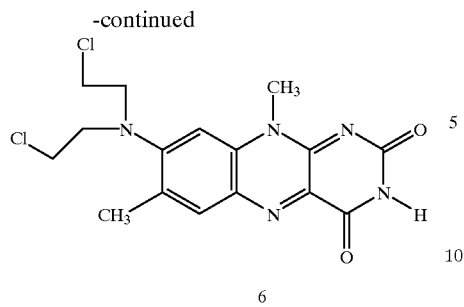

6

One of the chlorines from 6 will be replaced with W to impart water solubility to the compound.

Riboflavin methanol is synthesized by the method of McCormick and upon photolysis it will yield lumiflavine methanol 7.

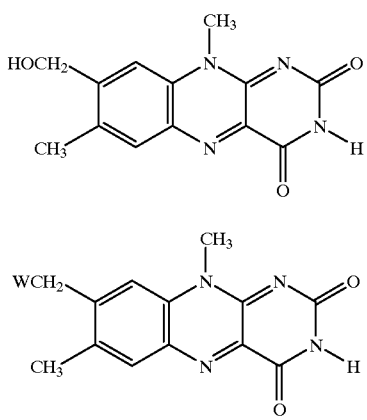

7

8

The hydroxyl group is replaced with a water soluble group (e.g., W, 8) as described earlier.

The N-3 (R2) of lumiflavine is alkylated using the method of P. Hemmerich (1964) Helv. Chim. Acta 47:464. This method is adapted to place water soluble groups at (R2) (e.g., 9).

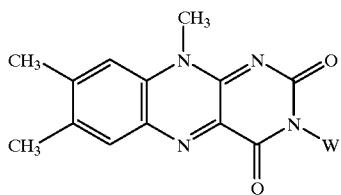

9

This lumiflavine will be water soluble, absorb visible light, and should not break down upon photolysis with visible light.

The corresponding series 10 and 11 are formed by application of known reactions.

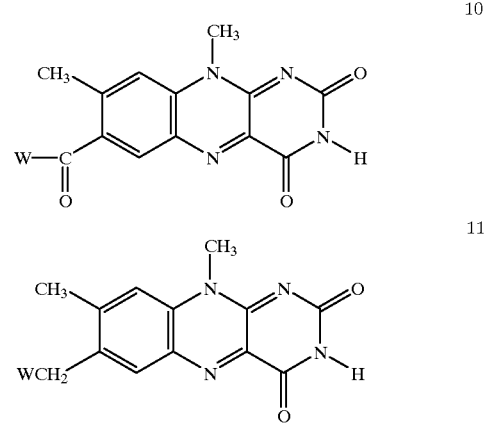

10

11

All compounds of this invention may be prepared by the methods above or by methods well known in the art, or by adapting the methods above or methods well known in the art. In addition, reactants specified herein may be substituted for others that produce a similar function.

Although the description above contains many specificities, these should not be construed as limiting the scope of the invention but as merely providing illustrations of some of the presently-preferred embodiments of this invention. Thus, the scope of the invention should be determined by the appended claims and their legal equivalents, rather than by the examples given.

What is claimed is:

1. A method for treating a fluid to neutralize microorganisms which may be present therein, said fluid containing one or more components selected from the group consisting of protein, blood, and blood constituents, said method comprising:

(a) adding to said fluid a neutralization-effective amount of a microorganism neutralizer of formula:

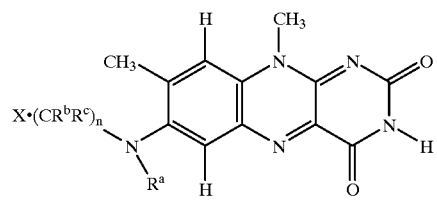

wherein X is a halogen selected from the group consisting of chlorine, bromine and iodine, $R^a$, $R^b$ and $R^c$ are, independently of each other, selected from the group consisting of hydrogen, optionally substituted hydrocarbyl, and halogen selected from the group consisting of chlorine, bromine and iodine, and n is an integer from 0 to 20;

(b) exposing the fluid of step (a) to a triggering event whereby said microorganisms are neutralized.

2. A method for treating a fluid to neutralize microorganisms which may be present therein, said fluid containing one or more components selected from the group consisting of protein, blood, and blood constituents, said method comprising:

(a) adding to said fluid a neutralization-effective amount of a microorganism neutralizer of formula:

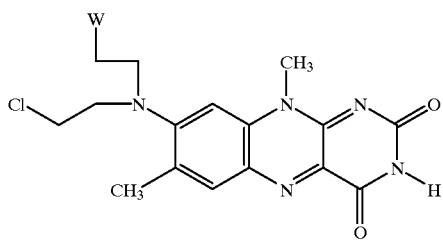

wherein W is a water soluble group;

(b) exposing the fluid of step (a) to a triggering event whereby said microorganisms are neutralized.

3. A non-toxic composition comprising a blood product additive photosensitizer for inactivating microrganisms suitable for administration to a patient having the structure

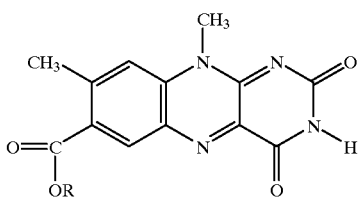

wherein R is selected from the group consisting of hydrogen and optionally substituted straight chain or branched alkyl having from 1 to 20 carbon atoms.

4. A non-toxic composition comprising a blood product additive photosensitizer for inactivating microrganisms suitable for administration to a patient having the structure

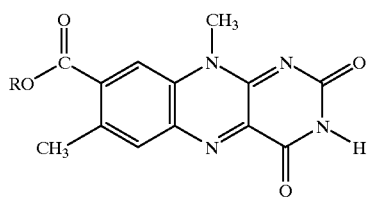

wherein R is selected from the group consisting of hydrogen and optionally substituted straight chain or branched alkyl having from 1 to 20 carbon atoms.

5. A non-toxic composition comprising a blood product additive photosensitizer for inactivating microrganisms suitable for administration to a patient having the structure:

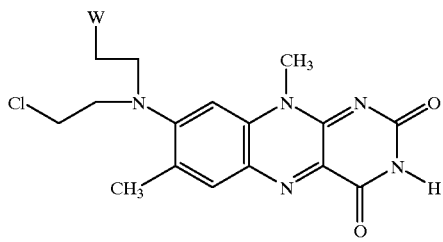

wherein W is a water soluble group.

6. A method of making a compound having structure:

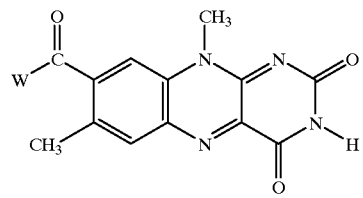

wherein W is a water soluble group, comprising:

(a) photolyzing carboxyriboflavin;

(b) reacting (a) with oxallylchloride;

(c) reacting (b) with a member of the group consisting of ascorbate, glucosamine, protected glucose derivatives, diethylene glycol and triethylene glycol.

7. A method of making a compound having the structure:

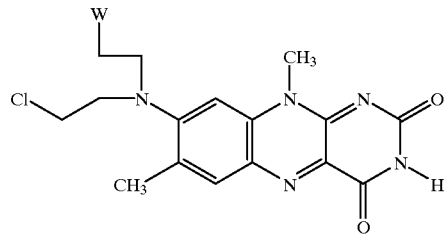

where W is a water soluble group, comprising:

(a) contacting

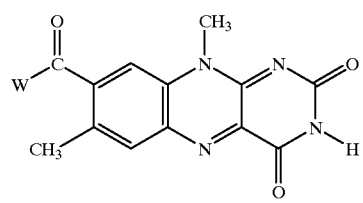

with sodium azide;

(b) reacting (a) with

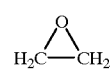

and $POCl_3$.

(c) reacting (b) with a water solubilizing group.

* * * * *